United States Patent
Hrakovsky

(10) Patent No.: US 9,186,333 B2
(45) Date of Patent: Nov. 17, 2015

(54) PROCESS FOR PREPARING PHARMACEUTICAL COMPOSITIONS OF FINGOLIMOD

(75) Inventor: Julia Hrakovsky, Rosh Ha-Ayin (IL)

(73) Assignee: Teva Pharmaceutical Industries Ltd., North Wales, PA (US)

( * ) Notice: Subject to any disclaimer, the term of this patent is extended or adjusted under 35 U.S.C. 154(b) by 0 days.

(21) Appl. No.: 13/564,362

(22) Filed: Aug. 1, 2012

(65) Prior Publication Data

US 2013/0034603 A1 Feb. 7, 2013

Related U.S. Application Data

(60) Provisional application No. 61/513,865, filed on Aug. 1, 2011.

(51) Int. Cl.
*A61K 9/48* (2006.01)
*A61K 9/14* (2006.01)
*A61K 31/137* (2006.01)

(52) U.S. Cl.
CPC .............. *A61K 9/485* (2013.01); *A61K 9/145* (2013.01); *A61K 9/146* (2013.01); *A61K 9/4858* (2013.01); *A61K 9/4866* (2013.01); *A61K 9/4883* (2013.01); *A61K 31/137* (2013.01)

(58) Field of Classification Search
None
See application file for complete search history.

(56) References Cited

U.S. PATENT DOCUMENTS

| 3,068,148 | A | * | 12/1962 | Freedman et al. | ............. 514/570 |
| 2002/0150614 | A1 | * | 10/2002 | Gergely et al. | ................ 424/449 |
| 2004/0143015 | A1 | * | 7/2004 | Villhauer | ...................... 514/563 |
| 2005/0069586 | A1 | * | 3/2005 | Hrakovsky et al. | ........... 424/464 |
| 2006/0275357 | A1 | * | 12/2006 | Oomura et al. | ................ 424/451 |
| 2008/0051397 | A1 | | 2/2008 | Esposito et al. | |
| 2008/0311188 | A1 | | 12/2008 | Oomura et al. | |
| 2009/0203798 | A1 | | 8/2009 | Oomura et al. | |
| 2010/0040678 | A1 | | 2/2010 | Ambuhl et al. | |

FOREIGN PATENT DOCUMENTS

| WO | 2009/048993 | | 4/2009 |
| WO | WO-2009-048993 | * | 4/2009 |
| WO | WO-2010-045601 | * | 4/2010 |
| WO | 2010/055028 | | 5/2010 |
| WO | WO 2011/131369 | | 10/2011 |
| WO | WO 2012/070059 | | 5/2012 |

OTHER PUBLICATIONS

International Search Report and Written Opinion for PCT/EP2012/049177, mailed on Oct. 4, 2012.

* cited by examiner

*Primary Examiner* — Frederick Krass
*Assistant Examiner* — Celeste A Roney
(74) *Attorney, Agent, or Firm* — Baker & Hostetler LLP

(57) ABSTRACT

The present invention provides a process for preparing a pharmaceutical composition of fingolimod comprising: (i) obtaining a intimate admixture comprising fingolimod or a pharmaceutically acceptable salt thereof, and at least one surfactant (wetting agent), e.g., an intimate admixture of the fingolimod and the at least one surfactant, and (ii) optionally combining the intimate admixture from step (i) with one or more excipients. Also provided are pharmaceutical compositions and dosage forms obtainable by the process, uses of the pharmaceutical compositions and dosage forms, and methods of treating appropriate diseases with the pharmaceutical compositions or dosage forms.

51 Claims, No Drawings

PROCESS FOR PREPARING PHARMACEUTICAL COMPOSITIONS OF FINGOLIMOD

This patent application claims the benefit of U.S. Provisional No. 61/513,865, filed 1 Aug. 2011, the disclosures of which are herein incorporated by reference.

The present invention relates to a process for preparing pharmaceutical compositions of fingolimod or pharmaceutically acceptable salts thereof. In particular, the present invention relates to the preparation of stable compositions which can be incorporated into a solid dosage form.

BACKGROUND OF THE INVENTION

Fingolimod is a sphingosine-1 phosphate (S1P) agonist, having immunosuppressive activity. Fingolimod, in the form of its hydrochloride salt has the following formula:

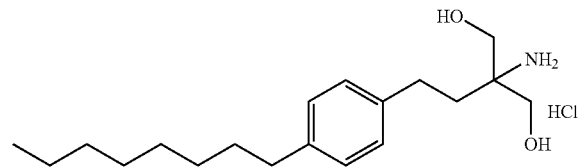 [SMILES: CCCCCCCCc1ccc(CCC(N)(CO)CO)cc1 ; Cl]

Fingolimod is currently marketed as an immediate release capsule for the treatment of multiple sclerosis. This formulation contains 0.5 mg equivalent of fingolimod base in the form of the hydrochloride salt.

WO2010/055028, US 20100040678, US 20060275357, US20090203798, US20080311188, WO2009/48993 disclose formulations containing inter alia fingolimod.

WO2010/055028 discloses crystalline forms and hydrates of fingolimod hydrochloride and pharmaceutical formulations thereof. The solid pharmaceutical formulations comprise the crystalline fingolimod hydrochloride and a sugar alcohol. The sugar alcohol can be, e.g. mannitol, maltitol, inositol, xylitol or lactitol.

US 20100040678 discloses rapidly disintegrating dosage forms of S1P agonists including FTY720 (fingolimod). The compositions comprise a coating, wherein the coating comprises one or more polymer resins and one or more metal oxides.

US 20060275357, US20080311188 and US20090203798 disclose pharmaceutical compositions of S1P agonists comprising a sugar alcohol, such as mannitol.

WO2009/048993 discloses dosage forms containing S1P modulators and one or more excipients selected from fillers, binders, disintegrants, lubricants, flow regulators, matrix formers, plasticizers, flavouring agents and sweeteners.

The applicant has discovered that certain S1P agonist compounds, and in particular, fingolimod, possess properties that can cause processing problems when preparing pharmaceutical formulations. In particular, it has been found that fingolimod particles have a strong tendency to stick to surfaces and to each other. Moreover, the applicant has found that there is a significant problem with achieving a desirable content uniformity in pharmaceutical formulations containing fingolimod. Further, fingolimod can react with certain excipients to produce degradation products in the final formulation. The present invention addresses the need to provide stable formulations of fingolimod that additionally have a desirable content uniformity by a simplified process.

The applicant has found that the stability and uniformity of pharmaceutical compositions containing fingolimod is heavily dependent on the choice of excipients used in the formulation, and the process by which the formulation is prepared.

SUMMARY OF THE INVENTION

The present invention provides a process for preparing a pharmaceutical composition of fingolimod comprising: (i) obtaining a intimate admixture comprising fingolimod or a pharmaceutically acceptable salt thereof, and at least one surfactant (wetting agent) e.g., an intimate admixture of the fingolimod and the at least one surfactant, and (ii) optionally combining the intimate admixture from step (i) with one or more excipients.

Also provided are pharmaceutical compositions and dosage forms obtainable by the process.

DETAILED DESCRIPTION OF THE INVENTION

As used herein, unless indicated otherwise, references to fingolimod include fingolimod in its free base form, or as a pharmaceutically acceptable salt, or solvates and hydrates of the free base or salt forms. Preferably the fingolimod is in the form of a pharmaceutically acceptable acid addition salt, and more preferably, the fingolimod is in the form of its hydrochloride salt.

As used herein, unless indicated otherwise, references to weight ratios of fingolimod are based on the equivalent free base weight of fingolimod.

As used herein, unless indicated otherwise, references to total weight of the pharmaceutical composition refers to the total weight of the active agent(s) and excipient(s) and excludes any capsule shell. Unless indicated otherwise, the total weight of the pharmaceutical composition refers to the weight of the pharmaceutical composition excluding any capsule shell.

As used herein the term "surfactant" is intended to mean a compound capable of changing the interface between liquid and solid, to reduce the surface tension of liquid. Thus the term "surfactants" includes those compounds known as surfactants and wetting agents.

As used herein the term "excipient" is intended to mean a pharmaceutically acceptable additive mixed with the active agent(s) in a pharmaceutical composition, wherein the term "excipient" excludes the at least one surfactant in the intimate admixture.

The term "intimate mixture" as used herein refers to a mixture of two or more solid components that are intimately mixed so as to comprise a mixture of closely packed components. An intimate admixture according to the present invention may be formed by any procedure that enables thorough blending of the particles of fingolimod and the at least one surfactant (wetting agent) so that the particles are in intimate contact or close association with each other. Examples of suitable processes for achieving an intimate admixture include co-blending, co-screening, co-compacting, co-compressing or a combination thereof. For example, the fingolimod and the excipient(s) can be mixed in high shear mixer, or pre-blended or triturated with a surfactant and screened using a manual or electrical screen. The resulting mixture does not require milling but can be subjected to a conical mill, ball mill, attrition mill, vibratory mill or oscillating granulator to effect deagglomeration without any significant particle size reduction of the drug particles, for example, when using Quadro Comil, by choosing a screen with a screen openings larger than the drug or the admixture particles.

The present invention is based on the findings that pharmaceutical compositions and dosage forms comprising fingolimod having improved stability and/or content uniformity and which can be easily manufactured by first preparing an intimate admixture comprising fingolimod and at least one surfactant, e.g., an intimate admixture of the fingolimod with one. surfactant. The intimate admixture can then be used as a premix for the preparation of a pharmaceutical preparation or dosage forms, for example by being combined with one or more additional pharmaceutically acceptable excipients.

Without wishing to be bound by any theory, it is believed that the at least one surfactant in step (i), when present in the intimate admixture with the fingolimod prevents the fingolimod particles from adhering to each other (and thus preventing the formation of agglomerates) or to the surface of the processing equipment, and further protects the drug from exposure to other excipients which can interact with the fingolimod to cause degradation.

Preferably, the intimate admixture consists essentially of fingolimod and at least one surfactant. In particular, the intimate admixture is substantially free of excipients other than the surfactant (wetting agent). For example, the intimate admixture is prepared in the absence of fillers, binders or diluents. Preferably, the intimate admixture is prepared in the absence of fillers, binders, lubricants, glidants, disintegrants or diluents. More preferably, the intimate admixture is a homogeneous mixture of the fingolimod or a pharmaceutically acceptable salt thereof and the at least one surfactant. When the intimate admixture comprises excipients (e.g., fillers, binders, lubricants, glidants disintegrants or diluents) other than the at least one surfactant, each excipient is preferably in a lower amount than the at least one surfactant, e.g., in an amount of less than about 0.2 to about 5 mg, preferably less than about 0.25 to about 1 mg, and more preferably less than about 0.5 mg, wherein the amount of the at least one surfactant is the combined amount of all the surfactant(s) used if more than one surfactant is used.

In a preferred embodiment, the intimate admixture in step (i) can be prepared by a process comprising co-blending, co-screening, co-compacting, co-compressing or a combination thereof. For example, the fingolimod and the at least one surfactant can be mixed in high shear mixer, or the fingolimod can be pre-blended or triturated with the at least one surfactant and screened using a manual or electrical screen.

The present invention enables the production of fingolimod compositions having good stability and content uniformity without the need to employ high ratios of the at least one surfactant. For example, the process of the invention preferably employs a weight ratio of the at least one surfactant to fingolimod (based on the free base weight) in step (i) of less than about 100:1, less than about 50:1, less than about 20:1, or less than about 10:1, wherein to determine the weight ratio the Weight of the at least one surfactant is the combined weight of all the surfactant(s) used if more than one surfactant is present in the intimate admixture. More preferably, the weight ratio of the at least one surfactant to fingolimod (based on the free base weight) is significantly less than 100:1, e.g. less than about 5:1, particularly less than about 2:1 and most preferably less than about 1.5:1.

In preferred embodiments, the weight ratio of the at least one surfactant to fingolimod (based on the free base weight) in the intimate admixture of step (i) is in the range of about 10:1 to about 0.2:1, about 9:1 to 0.2:1, about 8:1 to about 0.3:1, about 5:1 to about 0.4:1, about 2.5:1 to about 0.5:1, about 2:1 to about 0.5:1, about 1.5:1 to about 0.8:1, about 1.2:1 to about 0.8:1, or most preferably about 1:1.

In a preferred process according to the invention, the at least one surfactant in step (i) is preferably selected from sodium lauryl sulfate, docusate sodium, polysorbate, poloxamer, hypromellose, polyoxyethylene alkyl ether, meglumine and mixtures thereof. Most preferably the surfactant is in a solid form.

More preferably, the at least one surfactant in step (i) is selected from sodium lauryl sulfate, docusate sodium, polysorbate, poloxamer, polyoxyethylene alkyl ether and mixtures thereof.

Poloxamer and sodium lauryl sulphate or mixtures thereof are particularly preferred excipients for use in step (i) of the process. In an especially preferred embodiment, the intimate admixture in step (i) consists essentially of fingolimod (preferably in the form of fingolimod hydrochloride) and sodium lauryl sulfate.

The fingolimod can be employed in any suitable form, for example, as the free base, or solvates, or hydrates thereof. Preferably, however, the fingolimod is in the form of a pharmaceutically acceptable salt thereof, preferably wherein the pharmaceutically acceptable salt is an acid addition salt, and more preferably wherein the acid addition salt is selected from hydrochloride, hydrobromide, ascorbate, malate, maleate, fumarate, succinate, oxalate, phosphate, mandelate, adipate, L-aspartate, glutarate, DL-lactate, laurate, salicylate, tartrate, mesylate, citrate, benzoate, or solvates or hydrates thereof, or mixtures of the pharmaceutically acceptable salts or their solvates or hydrates.

Preferably, the fingolimod is in the form of the hydrochloride salt.

The intimate admixture from step (i) can be further processed into a pharmaceutical composition or dosage form by adding one or more excipients in addition to the surfactant. By ensuring that the fingolimod is first intimately mixed with a surfactant, the applicant has found that subsequent processing to form a pharmaceutical composition or dosage form is improved. In particular, the problem with fingolimod particles sticking to the processing equipment and to each other, and thus causing stability and blend uniformity problems is significantly reduced.

Thus, the intimate admixture from step (i) can be further combined with any customary pharmaceutical excipients and auxiliaries in order to produce a pharmaceutical composition or dosage form, such as diluent, glidant, disintegrant, binder and lubricant, or mixtures thereof.

Examples of suitable diluents (fillers) include dibasic calcium phosphate, microcrystalline cellulose, lactose, lactose monohydrate, mannitol, calcium carbonate, magnesium carbonate, sucrose, glucose, sorbitol, calcium sulfate, powdered cellulose, silicified microcrystalline cellulose, cellulose acetate, dextrates, dextrin, dextrose, ethylcelluose, fructose, glyceryl palmitostearate, lactitol, magnesium carbonate, magnesium oxide, maltodextrin, maltose, medium-chain triglycerides, starch and polydextrose.

Preferred diluents include those selected from dibasic calcium phosphate, microcrystalline cellulose, mannitol, calcium carbonate, magnesium carbonate, sorbitol, calcium sulfate, powdered cellulose, silicified microcrystalline cellulose, cellulose acetate, magnesium carbonate, magnesium oxide, starch and medium-chain triglycerides, or mixtures thereof.

Particularly preferred are diluents selected from dibasic calcium phosphate and microcrystalline cellulose or mixtures thereof. Dibasic calcium phosphate is a particularly preferred diluent.

The diluent can be used in an amount in the pharmaceutical composition of from about 50 to about 95 wt % (based on the total weight of the pharmaceutical composition), preferably about 60 to about 90 wt %, about 70 to about 90%, and particularly about 72 to about 88 wt %, and especially about 82 to about 88 wt %.

Examples of suitable glidants include colloidal silicon dioxide, cornstarch, talc or mixtures thereof.

Examples of suitable disintegrants include those selected from croscarmellose sodium, starch, crospovidone, sodium starch glycolate, alginic acid, calcium carboxymethylcellulose, sodium carboxymethylcellulose, calcium carboxymethylcellulose, powdered cellulose, chitosan, guar gum, magnesium aluminium silicate, methylcellulose, and sodium alginate, and mixtures thereof Examples of suitable binders include acacia, dextrin, povidone, hypromellose, hydroxypropyl cellulose, hydroxyethyl cellulose, polymethacrylates, methyl cellulose, ethyl cellulose, pregelatinized starch, gelatin, tragacanth, zein, or mixtures thereof. Preferably, the binder is selected from povidone, hypromellose, hydroxypropyl cellulose, hydroxyethyl cellulose, polymethacrylates, methyl cellulose, gelatin and ethyl cellulose or mixtures thereof.

Examples of suitable lubricants include magnesium stearate, sodium stearyl fumarate, stearic acid, glycerylbehenate, polyethylene glycols (preferably wherein the polyethylene glycol has a molecular weight of 6000 or more), polyoxyethylene stearate, magnesium lauryl sulfate, sodium oleate, and mixtures thereof.

The excipient in step (ii) can also include a glidant, such as those selected from: colloidal silicon dioxide, cornstarch, talc or mixtures thereof. Colloidal silicon dioxide is a particularly preferred glidant.

The glidant in step (ii) can be used in an amount of from about 0.5 about 10 wt % (based on the total weight of the pharmaceutical composition), preferably about 1 to about 8 wt %, about 3 to about 6%, particularly about 4 to about 5 wt %, and especially about 4 to about 4.5 wt %.

The excipient in step (ii) can also comprise a disintegrant. Examples of suitable disintegrants include those selected from croscarmellose sodium, starch, crospovidone, sodium starch glycolate, alginic acid, calcium carboxymethylcellulose, sodium carboxymethylcellulose, calcium carboxymethylcellulose, powdered cellulose, chitosan, guar gum, magnesium aluminium silicate, methylcellulose, and sodium alginate, and mixtures thereof.

Crospovidone, croscarmellose sodium, starch, and sodium starch glycolate, or mixtures thereof are particularly preferred, and crospovidone is an especially preferred disintegrant.

The disintegrant in step (ii) can be used in an amount of from about 2 about 20 wt % (based on the total weight of the pharmaceutical composition), preferably about 5 to about 15 wt %, about 5 to about 12%, and particularly about 7 to about 10 wt %.

The excipient in step (ii) may further include binder such as those selected from acacia, dextrin, povidone, hypromellose, hydroxypropyl cellulose, hydroxyethyl cellulose, polymethacrylates, methyl cellulose, ethyl cellulose, pregelatinized starch, gelatin, tragacanth, zein, or mixtures thereof. Preferably, the binder is selected from povidone, hypromellose, hydroxypropyl cellulose, hydroxyethyl cellulose, polymethacrylates, methyl cellulose, gelatin and ethyl cellulose or mixtures thereof. Povidone is a particularly preferred binder.

The binder in step (ii) can be used in an amount of from about 0.5 about 20 wt % (based on the total weight of the pharmaceutical composition), preferably about 1 to about 15 wt %, about 2 to about 10%, and particularly about 3 to about 6 wt %.

The excipient in step (ii) can further include a lubricant, such as those selected from magnesium stearate, sodium stearyl fumarate, stearic acid, glycerylbehenate, polyethylene glycols (preferably wherein the polyethylene glycol has a molecular weight of 6000 or more), polyoxyethylene stearate, sodium lauryl sulfate, magnesium lauryl sulfate, sodium oleate, and mixtures thereof. Preferred lubricants include those selected from magnesium stearate, sodium stearyl fumarate and mixtures thereof, with sodium stearyl fumarate being especially preferred.

The lubricant in step (ii) can be used in an amount of from about 0.3 about 5 wt % (based on the total weight of the pharmaceutical composition), preferably about 0.3 to about 2 wt %, and particularly about 0.5 to about 1 wt %.

Preferably, the excipient in step (ii) does not include a disintegrant. Particularly preferred excipients in step (ii) include a combination of at least one filler, at least one glidant, at least one lubricant, and optionally a binder. In an especially preferred embodiment of the present invention, excipient in step (ii) does not include a binder, hence, an especially preferred excipient combination for step (ii) is a mixture of a filler, glidant and a lubricant. An even more preferred excipient combination for step (ii) is a mixture of a diluent (filler) and a lubricant.

Preferred excipient combinations for the process include:

Step (i): Fingolimod (preferably fingolimod hydrochloride) and either sodium lauryl sulfate or poloxamer (preferably sodium lauryl sulfate), in the weight ratios as set out in any of the above embodiments.

Step (ii): At least one of each of a filler (preferably dibasic calcium phosphate and/or microcrystalline cellulose; more preferably dibasic calcium phosphate), glidant (preferably colloidal silicon dioxide or talc; more preferably colloidal silicon dioxide), lubricant (preferably magnesium stearate and/or sodium stearyl fumarate; more preferably sodium stearyl fumarate), binder (preferably povidone) and disintegrant (preferably crospovidone), and more preferably a combination of a filler, glidant and lubricant, in the weight ratios and concentrations as set out in any of the above embodiments.

More preferred excipient combinations for the process include:

Step (i): Fingolimod (preferably fingolimod hydrochloride) and either sodium lauryl sulfate or poloxamer (preferably sodium lauryl sulfate), in the weight ratios as set out in any of the above embodiments.

Step (ii): At least one of each of a diluent (preferably starch e.g. pregelatinized starch or maize starch) and a lubricant (preferably magnesium stearate and/or sodium stearyl fumarate; more preferably magnesium stearate), and more preferably a combination of a diluent and lubricant, in the weight ratios and concentrations as set out in any of the above embodiments.

Preferably, the weight ratio of the intimate admixture of step (i) to the excipients in step (ii) ranges from about 1:20 to about 1:70, more preferably 1:30 to about 1:60, and more preferably from about 1:40 to about 1:50.

Pharmaceutical compositions and dosage forms can be prepared by incorporating the excipients in step (ii) by any suitable process. For example, blending, dry mixing, wet granulation, or dry granulation. The mixture or granules can then be compressed to form tablets or filled into capsules [e.g. hard gelatine or HPMC (hydroxypropyl methyl cellulose) capsules], as desired. Preferably the pharmaceutical composition or dosage forms are prepared by incorporating the excipients in step (ii) by dry mixing, and filled into capsules or optionally compressed to form a tablet.

The present invention also encompasses pharmaceutical composition or dosage forms obtainable by the process described herein. Preferably the pharmaceutical compositions according to the invention are in a solid dosage forms. Preferably the dosage form is a tablet or capsule (preferably a filled hard gelatin or HPMC capsule). Preferably, dosage forms according to the invention comprise fingolimod or a pharmaceutically acceptable salt thereof, preferably fingolimod hydrochloride, in an amount of from about 0.2 to about 5 mg, preferably from about 0.25 to about 1 mg, and more preferably about 0.5 mg (based on the free base weight of fingolimod).

Advantageously, by using the process according to the present invention, stable pharmaceutical compositions of fingolimod having good blend uniformity can be prepared. Preferably, pharmaceutical compositions according to the invention have a stability such that after storage at 55° C. at 75% relative humidity for 7 days, the total amount of impurities and degradation products does not increase by more than 3.3%, preferably does not increase by more than 2.5%, and more preferably does not increase by more than 2% of the initial total amount of impurities and degradation products.

Also provided are pharmaceutical compositions or dosage forms of the invention are for use as an immunomodulator. More preferably, the pharmaceutical compositions or dosage forms are for use in the treatment of organ or tissue transplant rejection, graft versus host disease, inflammatory conditions, autoimmune disease or cancers, preferably for the treatment of multiple sclerosis.

The present invention further encompasses the use of the intimate admixture from step (i) as a premix for the preparation of a dosage form.

The present invention further provides the use of at least one surfactant to improve the stability and/or blend uniformity of a fingolimod composition. Preferably, the surfactant is in an intimate admixture with fingolimod or a pharmaceutically acceptable salt, solvate or hydrate thereof.

For the avoidance of doubt, additional embodiments of the present invention include those where each use of the term "comprising" is replaced with "consisting of" or "consisting essentially of" with such terms having their generally accepted meanings.

The present invention is illustrated by the following examples, which are not intended to limit the scope of the invention. It will be appreciated that various modifications are within the spirit and scope of the invention.

EXAMPLES

Comparative Example 1

Dosage forms having the composition as set out below in Table 1, were prepared by a dry mix method. The ingredients were blended for 15 minutes to form a final blend. The final blend was encapsulated into capsules.

TABLE 1

| Ingredient | Comp. Ex. 1 (R07405) mg/capsule |
| --- | --- |
| Part I | |
| Fingolimod HCl | 0.5 |
| Microcrystalline Cellulose | 50.0 |

TABLE 1-continued

| Ingredient | Comp. Ex. 1 (R07405) mg/capsule |
| --- | --- |
| Colloidal Silicon Dioxide | 1.0 |
| Hydrogenated Vegetable Oil | 5.5 |

Working Example 2

Fingolimod capsules having the composition as set out below were prepared by dry mixing using an intimate admixture as follows: Fingolimod particles are below 100 micron. Part I materials were triturated and screened through Quadro commil equipped with a 0.045 inch=1143 micron screen, blended with Part II materials and encapsulated into capsules. The materials of Parts I and II used are shown in Table 2.

TABLE 2

| Ingredient | Example 2 (R07407) mg/capsule |
| --- | --- |
| Part I | |
| Fingolimod HCl | 0.5 |
| Sodium Lauryl Sulfate | 0.5 |
| Part II | |
| Dibasic Calcium Phosphate | 40.0 |
| Colloidal Silicon Dioxide | 2.0 |
| Sodium Stearyl Fumarate | 4.5 |

A stability test was performed on each example by packing the capsules in plastic containers and storing them in the oven at 55° C. a 75% relative humidity. After 7 days storage, the total percentage of impurities and degradation products was measured. The results are displayed in Table 3 below.

TABLE 3

Results of Stability Tests

| | % Total Impurities* | |
| --- | --- | --- |
| Example | Initial (t = 0) | 7 days at 55° C. & 75% RH |
| 1 | 0.16 | 3.2 |
| 2 | 0 | 1.5 |

*Total percentage of impurities and degradation products were determined by HPLC. Sum of all quantified impurities and degradation products is reported as a total.

Working Example 3

| Ingredient | Example 3 (R-08887) mg/cap |
| --- | --- |
| Part I | |
| Fingolimod HCl | 0.56 |
| SLS | 0.56 |
| Part II | |
| Starch 1500 | 46.85 |
| Magnesium Stearate | 0.50 |
| Theoretical total Weight | 48.47 |

Fingolimod and SLS were triturated and screened manually through 30 mesh screen. Pregelatinized Starch (Starch 1500)

was screened through 30 mesh screen, added to the intimate Fingolimod/SLS mixture and blended in Y-Cone. Magnesium Stearate was screened through 50 mesh screen added to the Y-Cone and blended for additional 3 min.

API used for this trial has the particles less than 23 micron.

The invention claimed is:

1. A process for preparing a pharmaceutical composition of fingolimod comprising: first, (i) preparing an intimate admixture of fingolimod or a pharmaceutically acceptable salt thereof, with a solid surfactant that is selected from sodium lauryl sulfate, docusate sodium, polysorbate, poloxamer, hypromellose, polyoxyethylene alkyl ether, meglumine, and mixtures thereof, wherein when the intimate admixture comprises one or more excipients in addition to said solid surfactant, each of said excipients is present in an amount that is lower than the amount of the said solid surfactant, and, following step (i), (ii) combining the intimate admixture from step (i) with one or more excipients.

2. A process according to claim 1 wherein the intimate admixture in step (i) is obtained by a process comprising co-blending, co-screening, co-compacting, co-compressing or a combination thereof.

3. A process according to claim 1 wherein the intimate admixture in step (i) is obtained by a process without any significant particle size reduction of the drug particles.

4. A process according to claim 1 wherein the intimate admixture in step (i) is obtained by mixing the fingolimod or pharmaceutically acceptable salt thereof with the surfactant in a high shear mixer, or pre-blended or triturated with the surfactant and screened using a manual or electrical screen.

5. A process according to claim 1 wherein the weight ratio of the surfactant to fingolimod (based on the free base weight) in step (i) is less than about 100:1.

6. A process according to claim 5 wherein the weight ratio of the surfactant to fingolimod (based on the free base weight) in step (i) is less than about 50:1.

7. A process according to claim 5 wherein the weight ratio of the surfactant to fingolimod (based on the free base weight) in step (i) is less than about 10:1.

8. A process according to claim 5 wherein the weight ratio of the surfactant to fingolimod (based on the free base weight) in step (i) is less than about 2:1.

9. A process according to claim 1 wherein the weight ratio of the surfactant to fingolimod (based on the free base weight) in step (i) is in the range of about 10:1 to about 0.2:1.

10. A process according to claim 9 wherein the weight ratio of the surfactant to fingolimod (based on the free base weight) in step (i) is in the range of about 5:1 to about 0.4:1.

11. A process according to claim 9 wherein the weight ratio of the surfactant to fingolimod (based on the free base weight) in step (i) is in the range of about 1.5:1 to about 0.8:1.

12. A process according to claim 9 wherein the weight ratio of the surfactant to fingolimod (based on the free base weight) in step (i) is in the range of about 1.2:1 to about 0.8:1.

13. A process according to claim 9 wherein the weight ratio of the surfactant to fingolimod (based on the free base weight) in step (i) is about 1:1.

14. A process according to claim 1 wherein the surfactant in step (i) is selected from sodium lauryl sulfate, docusate sodium, polysorbate, poloxamer, polyoxyethylene alkyl ether, and mixtures thereof.

15. A process according to claim 1 wherein the surfactant in step (i) is sodium lauryl sulfate, polxamer or mixtures thereof.

16. A process according to claim 1 wherein the surfactant in step (i) is sodium lauryl sulfate.

17. A process according to claim 1 wherein the fingolimod is in the form of the free base, or a solvate, or hydrate thereof.

18. A process according to claim 1 wherein the fingolimod is in the form of a pharmaceutically acceptable salt thereof, a solvate or hydrate of the pharmaceutically acceptable salt, or mixtures of the pharmaceutically acceptable salts or their solvates or hydrates.

19. A process according to claim 18 wherein the fingolimod is in the form of the hydrochloride salt.

20. A process according to claim 1 wherein the one or more excipients are selected from a diluent, glidant, disintegrant, binder and lubricant, or a mixture thereof.

21. A process according to claim 20 wherein the diluent is selected from dibasic calcium phosphate, microcrystalline cellulose, lactose, lactose monohydrate, mannitol, calcium carbonate, magnesium carbonate, sucrose, glucose, sorbitol, calcium sulfate, powdered cellulose, silicified microcrystalline cellulose, cellulose acetate, dextrates, dextrin, dextrose, ethylcelluose, fructose, glyceryl palmitostearate, lactitol, magnesium carbonate, magnesium oxide, maltodextrin, maltose, medium-chain triglycerides, starch and polydextrose.

22. A process according to claim 20 wherein the diluent is selected from dibasic calcium phosphate, microcrystalline cellulose, mannitol, calcium carbonate, magnesium carbonate, sorbitol, calcium sulfate, powdered cellulose, silicified microcrystalline cellulose, cellulose acetate, magnesium carbonate, magnesium oxide, starch and medium-chain triglycerides, or mixtures thereof.

23. A process according to claim 20 wherein the diluent is selected from dibasic calcium phosphate, microcrystalline cellulose, starch or mixtures thereof.

24. A process according to claim 20 wherein the glidant is selected from: colloidal silicon dioxide, or cornstarch or talc or mixtures thereof.

25. A process according to claim 20 wherein the glidant is colloidal silicon dioxide.

26. A process according to claim 20 wherein the disintegrant is selected from croscarmellose sodium, starch, crospovidone, sodium starch glycolate, alginic acid, calcium carboxymethylcellulose, sodium carboxymethylcellulose, calcium carboxymethylcellulose, powdered or microcrystalline cellulose, chitosan, guar gum, magnesium aluminium silicate, methylcellulose, and sodium alginate, or mixtures thereof.

27. A process according to claim 20 wherein the disintegrant is selected from crospovidone, croscarmellose sodium, starch, and sodium starch glycolate, or mixtures thereof.

28. A process according to claim 20 wherein the disintegrant is crospovidone.

29. A process according to claim 20 wherein the binder is selected from acacia, dextrin, povidone, hypromellose, hydroxypropyl cellulose, hydroxyethyl cellulose, polymethacrylates, methyl cellulose, ethyl cellulose, pregelatinized starch, gelatin, tragacanth, zein, or mixtures thereof.

30. A process according to claim 20 wherein the binder is selected from povidone, hypromellose, hydroxypropyl cellulose, hydroxyethyl cellulose, polymethacrylates, methyl cellulose, gelatin and ethyl cellulose or mixtures thereof.

31. A process according to claim 20 wherein the binder is povidone.

32. A process according to claim 20 wherein the lubricant is selected from magnesium stearate, sodium stearyl fumarate, stearic acid, glycerylbehenate, polyethylene glycols, polyoxyethylene stearate, sodium lauryl sulfate, magnesium lauryl sulfate, sodium oleate, and mixtures thereof.

33. A process according to claim 20 wherein the lubricant is selected from magnesium stearate, sodium stearyl fumarate or mixtures thereof.

34. A pharmaceutical composition or dosage form prepared by a process according to claim 1.

35. A pharmaceutical composition according to claim 34 in a solid dosage form.

36. A dosage form according to claim 34 in the form of a tablet or capsule.

37. A dosage form according to claim 34 in the form of a filled hard gelatine or HPMC capsule.

38. A dosage form according to claim 34 comprising fingolimod or a pharmaceutically acceptable salt thereof in an amount of from about 0.2 to about 5 mg.

39. A dosage form according to claim 34 comprising fingolimod hydrochloride in an amount of about 0.5 mg.

40. A method of treatment of multiple sclerosis comprising administering a mammal in need thereof, a therapeutically effective amount of the pharmaceutical formulation or dosage form according to claim 34.

41. A method of preparing a dosage form comprising mixing the pharmaceutical composition prepared by the process of claim 1 as a premix with at least one other substance to form the dosage form.

42. A method of improving the stability and/or blend uniformity of a fingolimod composition by the use of a surfactant, said method comprising preparing an intimate admixture of said surfactant and fingolimod, followed by combining the preformed intimate admixture with one or more excipients to form said fingolimod composition, wherein said composition has increased stability or blend uniformity as compared to the same fingolimod composition not including said preformed intimate admixture of surfactant and fingolimod.

43. The method according to claim 42 wherein the surfactant is in an intimate admixture with fingolimod or a pharmaceutically acceptable salt, solvate or hydrate thereof.

44. The method according to claim 42 wherein the surfactant is selected from sodium lauryl sulfate, docusate sodium, polysorbate, poloxamer, hypromellose, polyoxyethylene alkyl ether, meglumine, and mixtures thereof.

45. The method according to claim 42 wherein the weight ratio of the surfactant to fingolimod (based on the free base weight) in the intimate admixture is about 1:1.

46. The method according to claim 42 wherein the intimate admixture is prepared by at least one of co-blending, co-screening, co-compacting or co-compressing a mixture of fingolimod and the surfactant.

47. The method according to claim 46 wherein the intimate admixture is prepared by co-blending a mixture of fingolimod and the surfactant, followed by screening.

48. The process of claim 18, wherein the pharmaceutically acceptable salt is an acid addition salt.

49. The process of claim 48, wherein the pharmaceutically acceptable salt is selected from hydrochloride, hydrobromide, ascorbate, malate, maleate, fumarate, succinate, oxalate, phosphate, mandelate, adipate, L-aspartate, glutarate, DL-lactate, laurate, salicylate, tartrate, mesylate, citrate, benzoate, or solvates or hydrates thereof.

50. A method of improving the stability, blend uniformity, or both of composition that includes fingolimod, comprising:
preparing an intimate admixture of fingolimod and a solid surfactant, wherein when the intimate admixture comprises one or more excipients other than said solid surfactant, each of said excipients is present in said intimate admixture in an amount that is less than the amount of the solid surfactant,
and,
subsequently combining the intimate admixture with one or more excipients to form said composition, wherein said composition has increased stability or blend uniformity as compared to the same fingolimod composition not including said preformed intimate admixture of surfactant and fingolimod.

51. A process according to claim 32, wherein the polyethylene glycol has a molecular weight of 6000 or more.

* * * * *